(12) United States Patent
Gupta et al.

(10) Patent No.: US 9,773,679 B2
(45) Date of Patent: Sep. 26, 2017

(54) METHOD OF ETCHING SEMICONDUCTOR STRUCTURES WITH ETCH GAS

(71) Applicant: American Air Liquide, Inc., Fremont, CA (US)

(72) Inventors: Rahul Gupta, Newark, DE (US); Venkateswara R. Pallem, Hockessin, DE (US); Vijay Surla, Newark, DE (US); Curtis Anderson, Victori, MN (US); Nathan Stafford, Damascus, OR (US)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 14/917,424

(22) PCT Filed: Sep. 9, 2014

(86) PCT No.: PCT/US2014/054780
§ 371 (c)(1),
(2) Date: Mar. 8, 2016

(87) PCT Pub. No.: WO2015/035381
PCT Pub. Date: Mar. 12, 2015

(65) Prior Publication Data
US 2016/0307764 A1    Oct. 20, 2016

Related U.S. Application Data

(60) Provisional application No. 61/875,321, filed on Sep. 9, 2013.

(51) Int. Cl.
B44C 1/22       (2006.01)
C03C 15/00      (2006.01)
(Continued)

(52) U.S. Cl.
CPC ........ *H01L 21/3065* (2013.01); *C07C 323/03* (2013.01); *H01L 21/02046* (2013.01);
(Continued)

(58) Field of Classification Search
None
See application file for complete search history.

(56) References Cited

U.S. PATENT DOCUMENTS 5,376,234 A    12/1994  Yanagida
5,431,777 A    7/1995   Austin et al.
(Continued)

FOREIGN PATENT DOCUMENTS

JP    H06 151384    5/1994
JP    H06 258815    9/1994
(Continued)

OTHER PUBLICATIONS

ExtremeTech, "New manufacturing technology enables vertical 3D NAND transistors, higher capacity SSDs," retrieved from the internet Jul. 25, 2016 at http://www.extremetec.com/computing/131777-new-manufacturing-technology-enables-vertical-3d-transistors-higher-capacity-ssds.
(Continued)

*Primary Examiner* — Stephanie Duclair
(74) *Attorney, Agent, or Firm* — Patricia E. McQueeney; Yan Jiang

(57) ABSTRACT

Disclosed are sulfur-containing compounds for plasma etching channel holes, gate trenches, staircase contacts, capacitor holes, contact holes, etc., in Si-containing layers on a substrate and plasma etching methods of using the same. The plasma etching compounds may provide improved selectivity between the Si-containing layers and mask material, less damage to channel region, a straight vertical profile, and reduced bowing in pattern high aspect ratio structures.

15 Claims, 13 Drawing Sheets

(51) Int. Cl.

| | |
|---|---|
| *C03C 25/68* | (2006.01) |
| *C23F 1/00* | (2006.01) |
| *H01L 21/302* | (2006.01) |
| *H01L 21/461* | (2006.01) |
| *H01L 21/3065* | (2006.01) |
| *H01L 21/306* | (2006.01) |
| *H01L 21/02* | (2006.01) |
| *H01L 21/311* | (2006.01) |
| *H01L 21/3213* | (2006.01) |
| *C07C 323/03* | (2006.01) |

(52) U.S. Cl.
CPC .. *H01L 21/30621* (2013.01); *H01L 21/31116* (2013.01); *H01L 21/32137* (2013.01)

(56) References Cited

U.S. PATENT DOCUMENTS

| | | | |
|---|---|---|---|
| 6,387,287 | B1 | 5/2002 | Hung et al. |
| 6,461,533 | B1 | 10/2002 | Horiike et al. |
| 7,645,707 | B2 | 1/2010 | Rusu et al. |
| 2003/0019841 | A1 | 1/2003 | Kesari et al. |
| 2009/0176375 | A1* | 7/2009 | Benson .................. C09K 13/00 438/719 |
| 2009/0212010 | A1* | 8/2009 | Wang ................ H01L 21/31116 216/47 |
| 2010/0264116 | A1* | 10/2010 | Suzuki ............. H01L 21/31116 216/67 |
| 2011/0180941 | A1 | 7/2011 | Hwang et al. |

FOREIGN PATENT DOCUMENTS

| | | |
|---|---|---|
| JP | H07 211694 | 8/1995 |
| JP | 3555737 | 8/2004 |
| JP | 3611723 | 1/2005 |
| KR | 10 2001 010568 | 2/2001 |

OTHER PUBLICATIONS

Haas, M.A. et al., "Darstellung und Eigneshcaftern von Trifluormethylmercaptothio-phosphoryldichlorid," Z. anorg. Allg. Chem., 501(6), Jun. 1983, 79-88, English Abstract.

James, R. et al., "The preparation of fluorinated cyclic sulphides and disulphides," Chemical Communications, 1969, 1274-1275.

Kim, J.K. et al., "Study on the etching characterisitics of amorphous carbon layer in oxygen plasma with carbonyl sulfide," J. Vac. Sci. Technol. A 31 (2), Mar./Apr. 2013.

Manos, D.M. et al., "Plasma etching: an introduction," Academic Press, Inc., Harcourt Brace Jovanovich, publishers, Boston, MA, 1989, 12-13.

Yu, S.-L. et al., "Oxidations of partially fluorinated alkyl sulfides. Preparation of methyl trifluoromethyl sulfoxide and methyl(trifluoromethyl)sulfur tetrafluroide," Inorganic Chemistry, vol. 13, No. 2, 1974, 484-486.

International Search Report and Written Opinion for corresponding PCT/US2014/054780, Dec. 16, 2014.

* cited by examiner

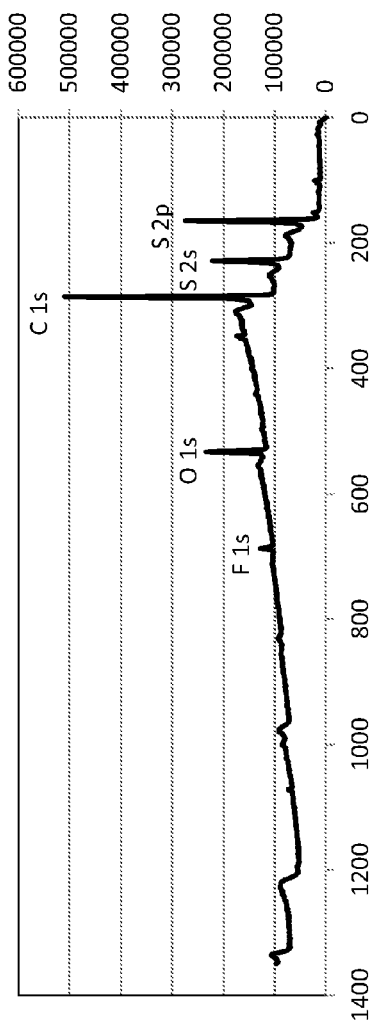
FIG 7
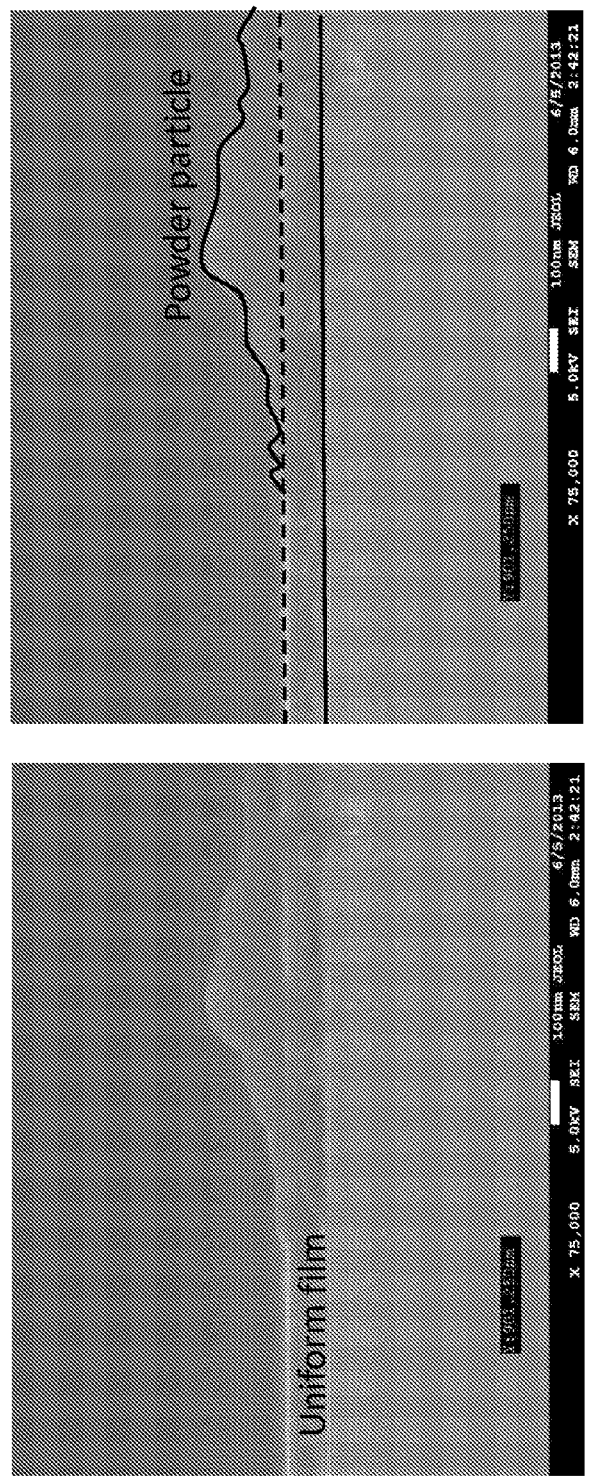
FIG 8A
FIG 8B

METHOD OF ETCHING SEMICONDUCTOR STRUCTURES WITH ETCH GAS

CROSS REFERENCE TO RELATED APPLICATIONS

The present application is a 371 of International PCT Application PCT/US2014/054780, filed Sep. 9, 2014, which claims the benefit of U.S. Provisional Application Ser. No. 61/875,321 filed Sep. 9, 2013, the contents of each being herein incorporated by reference in their entireties for all purposes.

TECHNICAL FIELD

Disclosed are sulfur-containing compounds for plasma etching channel holes, gate trenches, staircase contacts, capacitor holes, contact holes, etc., in Si-containing layers on a substrate and plasma etching methods of using the same.

BACKGROUND

In memory applications in the semiconductor industries, such as DRAM and 2D NAND, plasma etching removes silicon-containing layers, such as SiO or SiN layers, from semiconductor substrates. For novel memory applications, such as 3D NAND (US 2011/0180941), etching of stacks of multiple SiO/SiN or SiO/poly-Si layers is critical. Preferably, the etchant has high selectivity between the mask and layers being etched. Furthermore, the etchant preferably etches the structure such that the vertical profile is straight, with no bowing. The 3D NAND stack may include other silicon containing layers.

Traditionally, plasma etching is carried out using a plasma source which generates active species from a gas source (such as hydrogen-, oxygen-, or fluorine-containing gases). The active species then react with the Si-containing layers to form volatile species. The volatile species are removed by low pressure in the reactor, which is maintained by a vacuum pump. Preferably, the mask material is not etched by the active species. The mask material may comprise one of the following: photoresist, amorphous carbon (a-C), polysilicon (polySi), metals, or other hard masks that do not etch.

Traditional etch gases include $cC_4F_8$ (Octafluorocyclobutane), $C_4F_6$ (Hexafluoro-1,3-butadiene), $CF_4$, $CH_2F_2$, $CH_3F$, and/or $CHF_3$. These etch gases may also form polymers during etching. The polymer acts as protection or passivation layers on the sidewalls of the pattern etch structure. This polymer passivation layer prevents the ions and radicals from etching the sidewalls, which may cause non-vertical structures, bowing, and change of dimensions. It is well known in the art that selectivity and polymer deposition rate increases as the ratio of C:F increases (i.e., $C_4F_6 > C_4F_8 > CF_4$). See, e.g., U.S. Pat. No. 6,387,287 to Hung et al.

Traditional etch chemistries may not provide the high aspect ratio (>20:1) necessary in new applications due at least to insufficient polymer deposition on side walls during the plasma etching process. Additionally, $C_xF_y$ polymers on sidewalls are susceptible to etching. As a result, the etched patterns may not be vertical and structures may show bowing, change in dimensions, and/or pattern collapse.

Bowing may result from sidewall etching of the mask layer, which is often an amorphous carbon material. Amorphous carbon materials may be etched by oxygen radicals in the plasma which may cause increased opening of the mask and result in the bow-like, or angled/curved, etch structure.

Sulfur gases like COS (carbonyl sulfide) and $SO_2$ (sulfur dioxide) have been used in the past in combination with oxygen plasma to etch the amorphous carbon layer in the pattern etch process. The sulfur may provide a passivation layer on the amorphous carbon to help protect the surface from oxygen radicals and therefore help to prevent the bow-like structures. For example, Kim et al (J. Vac. Sci. Technol. A 31 (2), March/April 2013) disclose that a 50 nm amorphous carbon hole etched in a gas mixture of $O_2$ and 5% COS produce a more anisotropic etch profile and improved the top/bottom opening ratio by about 37% as compared to those etched without COS.

Rusu et al (U.S. Pat. No. 7,645,707) describe the process of etching a dielectric layer using an etchant gas comprising a fluorine component, $O_2$, and a sulfur component gas The sulfur component gas is preferably $H_2S$, COS or $CS_2$.

Yanagida (U.S. Pat. No. 5,376,234) discloses a dry etching method wherein one compound selected from mercaptan, thioether and disulfide each having a fluorocarbon side chain is used as a main component of the etching gas. Examples in which $C_2F_6S_2$ is used to etch a $SiO_2$ interlayer insulation film are provided.

US2003/0019841 to Behr et al. discloses the addition of perfluorochemicals, such as $CF_3SF_5$, to a cleaning or etching gas.

KR10-2001/010568 to Samsung Electronics Co. Ltd. discloses dry etching of oxide films using sulfur-containing fluorocarbon gases, such as $C_4F_8S$, $C_3F_6S$, and $C_3F_6S_2$.

Molecules containing thiocarbonyl groups (>C=S) and fluorine atoms have also been proposed for different etch processes. See, e.g., JP06-151384, JP06-258815, and JP07-211694 to Sony Corp.

A need remains for new etch gas compositions for use in plasma applications.

NOTATION AND NOMENCLATURE

Certain abbreviations, symbols, and terms are used throughout the following description and claims, and include:

As used herein, the indefinite article "a" or "an" means one or more.

As used herein, the terms "approximately" or "about" mean±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x (NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms and the term "fluoroalkyl group" refers to saturated functional groups containing exclusively carbon and fluorine and optionally hydrogen (i.e., the fluoroalkyl group may be partially or fully fluorinated). Further, the term "alkyl group" and "fluoroalkyl group" refers to linear, branched, or cyclic groups. Examples of linear alkyl groups include without limitation, methyl groups, ethyl groups, propyl groups, butyl groups, etc. Examples of linear fluoroalkyl groups including $CF_3$—, $CF_2H$—, —$CF_2$—$CF_3$ or —CFH—CF3. Examples of branched alkyls groups include without limitation, t-butyl. Examples of cyclic alkyl groups include without limitation, cyclopropyl groups, cyclopentyl groups, cyclohexyl groups, etc. Cyclic groups and compounds are designated by "c" before the formula and "—" at opposite ends of the cycle (i.e., c(—$CH_2$—CH—$CH_2$—) would be a cyclopropyl group and c(—$CH_2$—$CH_2$—$CH_2$—) would be cyclopropane).

As used herein, the term "etch" or "etching" refers to a plasma etch process (i.e., a dry etch process) in which ion bombardment accelerates the chemical reaction in the vertical direction so that vertical sidewalls are formed along the edges of the masked features at right angles to the substrate (Manos and Flamm, Plasma Etching An Introduction, Academic Press, Inc. 1989 pp. 12-13). The etching process produces apertures, such as vias, trenches, channel holes, gate trenches, staircase contacts, capacitor holes, contact holes, etc., in the substrate.

The term "pattern etch" or "patterned etch" refers to etching a non-planar structure, such as a patterned mask layer on a stack of silicon-containing layers.

The term "selectivity" means the ratio of the etch rate of one material to the etch rate of another material. The term "selective etch" or "selectively etch" means to etch one material more than another material, or in other words to have a greater or less than 1:1 etch selectivity between two materials.

As used herein, the abbreviation "NAND" refers to a "Negated AND" or "Not AND" gate; the abbreviation "2D" refers to 2 dimensional gate structures on a planar substrate; the abbreviation "3D" refers to 3 dimensional or vertical gate structures, wherein the gate structures are stacked in the vertical direction; and the abbreviation "DRAM" refers to Dynamic Random-Access Memory.

The standard abbreviations of the elements from the periodic table of elements are used herein. It should be understood that elements may be referred to by these abbreviations (e.g., S refers to sulfur, Si refers to silicon, H refers to hydrogen, etc.).

The unique CAS registry numbers (i.e., "CAS") assigned by the Chemical Abstract Service are provided to help better identify the molecules disclosed.

Please note that the Si-containing films, such as SiN and SiO, are listed throughout the specification and claims without reference to their proper stoichiometry. The silicon-containing layers may include pure silicon (Si) layers, such as crystalline Si, polysilicon (polySi or polycrystalline Si), or amorphous silicon; silicon nitride ($Si_kN_l$) layers; or silicon oxide ($Si_nO_m$) layers; or mixtures thereof, wherein k, l, m, and n, inclusively range from 1 to 6. Preferably, silicon nitride is $Si_kN_l$, where k and l each range from 0.5 to 1.5. More preferably silicon nitride is $Si_1N_1$. Preferably silicon oxide is $Si_nO_m$, where n ranges from 0.5 to 1.5 and m ranges from 1.5 to 3.5. More preferably, silicon oxide is $SiO_2$ or $SiO_3$. The silicon-containing layer could also be a silicon oxide based dielectric material such as organic based or silicon oxide based low-k dielectric materials such as the Black Diamond II or III material by Applied Materials, Inc. The silicon-containing layers may also include dopants, such as B, C, P, As and/or Ge.

SUMMARY

Disclosed are methods for plasma etching a silicon-containing layer on a substrate. The vapor of a compound is introduced into a chamber containing the silicon-containing layer on a substrate. The compound has a formula selected from the group consisting of $R^1$—SH $R^2$—S—$R^3$ $C_2F_4S_2$ (CAS 1717-50-6)

wherein $R^1$, $R^2$, and $R^3$ are each independently a saturated C1 to C4 alkyl or fluoroalkyl group and $R^2$ and $R^3$ may be joined to form a 5 or 6 member S-containing ring. An inert gas is introduced into the chamber. Plasma is generated to produce an activated vapor from the vapor. The activated vapor selectively reacts with the silicon-containing layer to form volatile by-products. Volatile by-products are removed from the chamber. The disclosed methods may include one or more of the following aspects:

- the compound being $C_2F_4S_2$ (CAS 1717-50-6);
- the compound having the formula $R^1$—SH;
- the compound being $F_3C$—SH (CAS 1493-15-8);
- the compound being $F_3C$—$CF_2$—SH (CAS 1540-78-9);
- the compound being $F_3C$—$CH_2$—SH (CAS 1544-53-2);
- the compound being $CHF_2$—$CF_2$—SH (CAS 812-10-2);
- the compound being $CF_3$—$CF_2$—$CH_2$—SH (CAS 677-57-6);
- the compound being $F_3C$—CH(SH)—$CF_3$ (CAS 1540-06-3);
- the compound having the formula $R^2$—S—$R^3$;
- the compound being $F_3C$—S—$CF_3$ (CAS 371-78-8);
- the compound being $F_3C$—S—$CHF_2$ (CAS 371-72-2);
- the compound being $F_3C$—$CF_2$—S—$CF_2$—$CF_3$ (CAS 155953-22-3);
- the compound being $F_3C$—$CF_2$—$CF_2$—S—$CF_2$—$CF_2$—$CF_3$ (CAS 356-63-8);
- $R^2$ and $R^3$ being joined to form a 5 to 6 member S-containing ring;
- the compound being c(—S—$CF_2$—$CF_2$—CHF—$CF_2$—) (CAS 1035804-79-5);
- the compound being c(—S—$CF_2$—CHF—CHF—$CF_2$—) (CAS 30835-84-8);
- the compound being c(—S—$CF_2$—$CF_2$—$CF_2$—$CF_2$—$CF_2$—) (CAS 24345-52-6);
- the compound being c(—S—CFH—$CF_2$—$CF_2$—CFH—)(2 R, 5 R) (CAS 1507363-75-8);
- the compound being c(—S—CFH—$CF_2$—$CF_2$—CFH—)(2 R, 5 S) (CAS 1507363-76-9);
- the compound being c(—S—CFH—$CF_2$—$CF_2$—$CH_2$—) (CAS 1507363-77-0);
- the inert gas being selected from the group consisting of He, Ar, Xe, Kr, Ne, and combinations thereof;
- the inert gas being Ar;
- mixing the vapor and the inert gas prior to introduction to the chamber to produce a mixture;
- introducing the vapor into the chamber separately from the inert gas;
- the mixture comprising between approximately 50% v/v and approximately 95% v/v inert gas;
- continuously introducing the inert gas to the chamber and introducing the vapor to the chamber in pulses;
- introducing an oxidizer into the chamber;
- not introducing an oxidizer into the chamber;
- the oxidizer being selected from the group consisting of $O_2$, $O_3$, CO, $CO_2$, NO, $N_2O$, $NO_2$, and combinations thereof;
- mixing the vapor and the oxidizer prior to introduction to the chamber;

introducing the vapor into the chamber separately from the oxidizer;
introducing the oxidizer continuously to the chamber and introducing the vapor to the chamber in pulses;
introducing into the chamber approximately 5% v/v to approximately 100% v/v of oxidizer;
the silicon-containing layer comprising a layer of silicon oxide, silicon nitride, polysilicon, or combinations thereof;
the silicon-containing layer further comprising oxygen atoms, nitrogen atoms, carbon atoms, or combinations thereof;
the silicon-containing layer not comprising silicon carbide;
the silicon-containing layer being a silicon oxide layer;
selectively etching the silicon oxide layer from an amorphous carbon layer;
selectively etching the silicon oxide layer from a photoresist layer;
selectively etching the silicon oxide layer from a polysilicon layer;
selectively etching the silicon oxide layer from a metal contact layer;
selectively etching the silicon oxide layer from a SiN layer;
the silicon-containing layer being a silicon nitride layer;
selectively etching the silicon nitride layer from an amorphous carbon layer;
selectively etching the silicon nitride layer from a patterned photoresist layer;
selectively etching the silicon nitride layer from a polysilicon layer;
selectively etching the silicon nitride layer from a metal contact layer;
selectively etching the silicon nitride layer from a SiO layer;
producing an aperture in the silicon-containing layer having an aspect ratio between approximately 10:1 and approximately 100:1;
producing a gate trench;
producing a staircase contact;
producing a channel hole;
producing a channel hole having an aspect ratio between approximately 60:1 and approximately 100:1;
producing a channel hole having a diameter ranging from approximately 40 nm to approximately 50 nm;
introducing an etching gas into the chamber;
the etching gas being selected from the group consisting of $cC_5F_8$, $cC_4F_8$, $C_4F_8$, $C_4F_6$, $CF_4$, $CHF_3$, $CF_3H$, $CH_2F_2$, COS, $CS_2$; $CF_3I$; $C_2F_3I$; $C_2F_5I$; $SO_2$; trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); and hexafluorocyclobutane (cis-1,1,2,2,3,4);
the etching gas being $cC_5F_8$;
the etching gas being $cC_4F_8$;
the etching gas being $C_4F_6$;
mixing the vapor and the etching gas prior to introduction to the chamber;
introducing the vapor into the chamber separately from the etching gas;
introducing approximately 1% v/v to approximately 99.9% v/v of the etching gas into the chamber;
activating the plasma by a RF power ranging from approximately 25 W to approximately 10,000 W;
the chamber having a pressure ranging from approximately 1 mTorr to approximately 10 Torr;
introducing the vapor to the chamber at a flow rate ranging from approximately 0.1 sccm to approximately 1 slm;
maintaining the substrate at a temperature ranging from approximately −196° C. to approximately 500° C.;
maintaining the substrate at a temperature ranging from approximately −120° C. to approximately 300° C.;
maintaining the substrate at a temperature ranging from approximately −10° C. to approximately 40° C.;
maintaining the substrate at a temperature ranging from approximately −100° C. to approximately 50° C.;
measuring the activated vapor by Quadropole mass spectrometer, optical emission spectrometer, FTIR, or other radical/ion measurement tool;
generating the plasma being by applying RF power.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 1a is a diagram showing polymer deposited on the sidewall during etching in a NAND stack;

FIG. 7 is a X-ray photoelectron spectroscopy (XPS) graph of the atoms in a polymer deposited from $C_2H_3F_3S$;

FIG. 8A is a Scanning Electron Microscope (SEM) picture of the polymer film deposited by $C_2H_3F_3S$;

FIG. 8B is the same SEM picture of the polymer film deposited by $C_2H_3F_3S$ with the addition of lines to better mark the boundaries of each layer;

DESCRIPTION OF PREFERRED EMBODIMENTS

Figure 1:
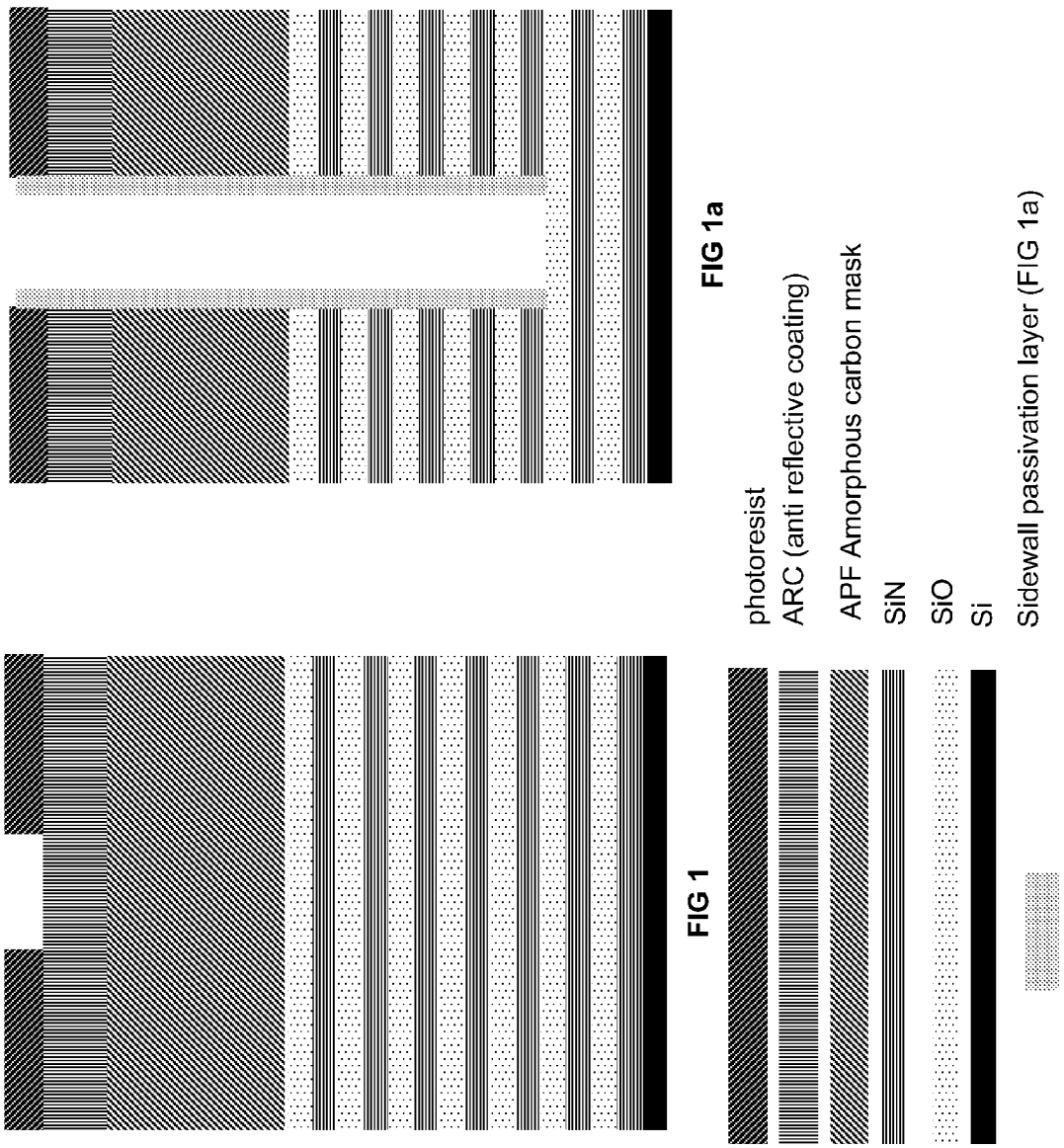
FIG. 1 is a diagram showing exemplary layers in a NAND stack.

Disclosed are sulfur-containing compounds for plasma etching channel holes, gate trenches, staircase contacts, capacitor holes, contact holes, etc., in silicon-containing layers. The disclosed etching compounds may provide higher selectivity to mask layers and no profile distortion in high aspect ratio structures.

The plasma etching compounds may provide improved selectivity between the Si-containing layers and mask materials, less damage to channel region, and reduced bowing in pattern high aspect ratio structures. The plasma etching compounds may also etch through alternating layers of polySi, SiO, and/or SiN, resulting in a vertical etch profile.

The disclosed sulfur-containing compounds have one of the following formulae:

wherein $R^1$, $R^2$, and $R^3$ is each independently a saturated C1 to C4 alkyl or fluoroalkyl group and $R^2$ and $R^3$ may be joined to form a 5 or 6 member S-containing ring.

In one alternative, the sulfur-containing compound is $C_2F_4S_2$ (CAS 1717-50-6). This compound is commercially available. Applicants believe that the cyclic structure of this compound will produce fragments during the plasma process that are suitable for both anisotropically etching the Si-containing layer and depositing a S-containing polymer passivation layer on the sidewalls of the structure being etched (see FIG. 1a).

In another alternative, the compound has the formula $R^1$—SH, wherein $R^1$ is a saturated C1 to C4 alkyl or fluoroalkyl group. These compounds may be commercially available or synthesized in one-step method by reduction of the corresponding sulfenyl chlorides by an excess of hydrogen sulfide in an autoclave at room temperature (see, e.g., Bekker et al., Phosphorus, Sulfur, and Silicon and the Related Elements (1996) 119, 161-68). Alternatively, $R^1$—S—Cl and $Cl_2$—P—O—$CH_3$ may be reacted in a 2-step process with $PSCl_3$ followed by $H_2O$ (see, e.g., Haas and Kortmann, Zeitschrift fuer Anorganische and Allgemeine Chemie, 501, 79-88, 1983).

Applicants believe that the terminal SH of $R^1$—SH provides lighter S-containing fragments in the plasma, permitting the S-containing polymer to deposit the passivation layer on the sidewalls of the structure being etched (see FIG. 1a) more effectively during the etch process, thereby protecting the integrity of the hardmask profile and leading to an etch profile that is desired. The presence of H in the S-containing polymer passivation layer may also strengthen the polymer, making it more resistant to damage from the etching environment than layers containing less H. Exemplary compounds having the formula $R^1$—SH include $F_3CSH$ (CAS 1493-15-8), $F_3C$—$CF_2$—SH (CAS 1540-78-9), $F_3C$—$CH_2$—SH (CAS 1544-53-2), $CHF_2$—$CF_2$—SH (CAS 812-10-2), $CF_3$—$CF_2$—$CH_2$—SH (CAS 677-57-6), and $F_3C$—CH(SH)—$CF_3$ (CAS 1540-06-3).

In another alternative, the compound has the formula $R^2$—S—$R^3$, wherein $R^2$ and $R^3$ is each independently a saturated C1 to C4 alkyl or fluoroalkyl group and $R^2$ and $R^3$ may be joined to form a 5 or 6 member S-containing ring. Applicants believe that S being in its +2 oxidation state in these molecules provides a better ability to produce fragments suitable for formation of the sidewall polymer passivation layer than those produced from compounds having S in higher oxidation states. The combination of one sulfur atom with two or more carbon atoms in the R2-S—R3 molecule may also produce a carbon rich S-containing polymer passivation layer that may better protect the sidewall from damage during the etch process.

Exemplary linear molecules having the formula $R^2$—S—$R^3$ include $F_3C$—S—$CF_3$ (CAS 371-78-8), $F_3C$—S—$CHF_2$ (CAS 371-72-2), $F_3C$—$CF_2$—S—$CF_2$—$CF_3$ (CAS 155953-22-3), and $F_3C$—$CF_2$—$CF_2$—S—$CF_2$—$CF_2$—$CF_3$ (CAS 356-63-8). These compounds may be commercially available or synthesized by reacting $Hg(SCF_3)_2$ with MeI (see, e.g., Yu et al., Inorganic Chemistry (1974), 13(2), 484-6). Alternatively, the compound may be synthesized by photolysis of $CF_3SOC(O)Me$ (see, id.).

Exemplary cyclic molecules having the formula $R^2$—S—$R^3$ include c(—S—$CF_2$—$CF_2$—CHF—$CF_2$—) (CAS 1035804-79-5), c(—S—$CF_2$—CHF—CHF—$CF_2$—) (CAS 30835-84-8), c(—S—$CF_2$—$CF_2$—$CF_2$—$CF_2$—$CF_2$—) (CAS 24345-52-6), c(—S—CFH—$CF_2$—$CF_2$—CFH—)(2 R, 5 R) (CAS 1507363-75-8), c(—S—CFH—$CF_2$—$CF_2$—CFH—)(2 R, 5 S) (CAS 1507363-76-9), and c(—S—CFH—$CF_2$—$CF_2$—$CH_2$—) (CAS 1507363-77-0). These compounds may be synthesized by fluorinating the analogous unsaturated S-containing ring structure with potassium tetrafluorocobaltate (III) (see, e.g., Coe, e-EROS Encyclopedia of Reagents for Organic Synthesis, No pp. given; 2001). Alternatively, these compounds may be synthesized by vacuum pyrolysis of copolymers of unit structures —$(CF_2)_mS(CF_2)_nS$—. The —$(CF_2)_mS(CF_2)_nS$— copolymers may be produced by reacting $F_2C:CF_2$ with $CSF_2$ or tetrafluorothiirane. (see, e.g., James and Rowsell, Journal of the Chemical Society [Section] D: Chemical Communications (1969)(21), 1274-5).

The disclosed sulfur-containing plasma etch compounds are provided at between approximately 99.9% v/v and approximately 100.0% v/v purity, preferably between approximately 99.99% v/v and approximately 100.00% v/v purity, and more preferably between approximately 99.999% v/v and approximately 100.000% v/v purity. The disclosed etch compounds contain between approximately 0.0% by volume and approximately 0.1% by volume trace gas impurities with between approximately 0 ppm by volume to approximately 150 ppm by volume of nitrogen-containing and oxygen-containing gases, such as $N_2$ and/or $H_2O$ and/or HF and/or $H_2S$ and/or $CO_2$ and/or CO, and/or $SO_2$ contained in said trace gaseous impurities. Preferably, the water content in the plasma etch compound is between approximately 0 ppm by weight and approximately 20 ppm by weight. The purified product may be produced by distillation and/or passing the gas or liquid through a suitable adsorbent, such as a 4 A molecular sieve.

In one alternative the disclosed plasma etch compounds contains between approximately 0% v/v and approximately 5% v/v, preferably between approximately 0% v/v and approximately 1% v/v, more preferably between approximately 0.0% v/v and approximately 0.1% v/v, and even more preferably between approximately 0.00% v.v. and approximately 0.01% v/v of any of its isomers. This alternative may provide better process repeatability. This alternative may be produced by distillation of the gas or liquid. Alternatively, the disclosed plasma etch compounds may contain between approximately 5% v/v and approximately 50% v/v of one or more of its isomers, particularly when the isomer mixture provides improved process parameters or isolation of the target isomer is too difficult or expensive. For example, a mixture of isomers may reduce the need for two or more gas lines to the plasma reactor. One exemplary mixture may combine 50% v/v $F_3C-CF_2-SH$ (CAS 1540-78-9) with 50% v/v $F_3C-S-CHF_2$ (CAS 371-72-2) or 90% c(—S—CFH—$CF_2$—$CF_2$—CFH—) (2 R, 5 R) (CAS 1507363-75-8) with 10% c(—S—CFH—$CF_2$—$CF_2$—CFH—)(2 R, 5 S) (CAS 1507363-76-9).

The disclosed compounds are suitable for plasma etching channel holes, gate trenches, staircase contacts, capacitor holes, contact holes, etc., in one or more Si-containing layers and compatible with the current and future generation of mask materials because they induce little to no damage on the mask along with good profile of high aspect ratio structures. In order to achieve those properties, the S atoms contained in the disclosed compounds may deposit an etch-resistant polymer layer during etching and help reduce the direct impact of the oxygen and fluorine radicals during the etching process. The disclosed compounds may also reduce damage to poly-Si channel structure during etching (see US 2011/0180941). Preferably, the S-containing compound is both suitably volatile and stable during the etching process for delivery into the reactor/chamber.

Material compatibility tests are important to determine if any of the S-containing compounds will react with the chamber materials and degrade its performance with short term or long term use. Key materials involved in parts of chamber, valves, etc. include Stainless Steel, Aluminum, Nickel, PCTFE, PVDF, PTFE and other metals and polymers. At times these materials are exposed to higher temperatures and pressures which may enhance their degradation. The metrology methods may include visual inspection, weight measurement, measuring nanometer scale changes in SEM, tensile strength, hardness, etc.

The disclosed sulfur-containing compounds may be used to plasma etch silicon-containing layers on a substrate. The disclosed plasma etching method may be useful in the manufacture of semiconductor devices such as NAND or 3D NAND gates or Flash or DRAM memory. The other areas of applications include its use in different front end of the line (FEOL) and back end of the line (BEOL) etch applications. Additionally, it may also include etching Si for 3D TSV (Through Silicon Via) etch applications for interconnecting memory substrates on logic substrates.

The plasma etching method includes providing a reactor having a substrate disposed therein. The reactor may be any enclosure or chamber within a device in which etching methods take place such as, and without limitation, Reactive Ion Etching (RIE), Dual Capacitively Coupled Plasma with single or multiple frequency RF sources, Inductively Coupled Plasma (ICP), or Microwave Plasma reactors, or other types of etching systems capable of selectively removing a portion of the Si containing layer or generating active species. One of ordinary skill in the art will recognize that the different reactor designs provide different electron temperature control. Suitable commercially available reactors include but are not limited to the Applied Materials magnetically enhanced reactive ion etcher sold under the trademark eMAX™ or the Lam Research Dual CCP reactive ion etcher Dielectric etch product family sold under the trademark 2300® Flex™.

The reactor may contain one or more than one substrate. For example, the reactor may contain from 1 to 200 silicon wafers having from 25.4 mm to 450 mm diameters. Alternatively, the S-containing compounds may be used to remove Si-containing substrates from the reactor walls. A substrate is generally defined as the material on which a process is conducted. The substrates may be any suitable substrate used in semiconductor, photovoltaic, flat panel or LCD-TFT device manufacturing. Typically the substrate will be a patterned substrate having multiple layers thereon. Examples of suitable layers include without limitation silicon (such as amorphous silicon, polysilicon, crystalline silicon, any of which may further be p-doped or n-doped), silica, silicon nitride, silicon oxide, silicon oxynitride, tungsten, titanium nitride, tantalum nitride, mask materials such as amorphous carbon, antireflective coatings, photoresist materials, or combinations thereof. Additionally, layers comprising tungsten or noble metals (e.g. platinum, palladium, rhodium or gold) may be used.

The substrate may include a stack of multiple layers thereon similar to those shown in FIG. 1. In FIG. 1, a stack of seven SiO/SiN layers is located on top of a silicon wafer substrate (i.e., ONON or TCAT technology). One of ordinary skill in the art will recognize that some technologies replace the SiN layers with polySi layers (i.e., SiO/polySi or P-BIOS technology). An amorphous carbon mask layer is located on top of the seven SiO/SiN layers. An antireflective coating layer is located on top of the amorphous carbon mask. A pattern photoresist layer is located on top of the antireflective coating. The stack of layers in FIG. 1 reflects layers similar to those used to produce a 3D NAND gate. One of ordinary skill in the art will recognize that the stack of layers in FIG. 1 is provided for exemplary purposes only and that the disclosed sulfur-containing compounds may be used to etch other stacks of layers. Furthermore, one of ordinary skill in the art will recognize that the number SiO/SiN or SiO/poly-Si layers in the stack may vary (i.e., may include more or less than the seven SiO/SiN layers depicted)

Figure 2:
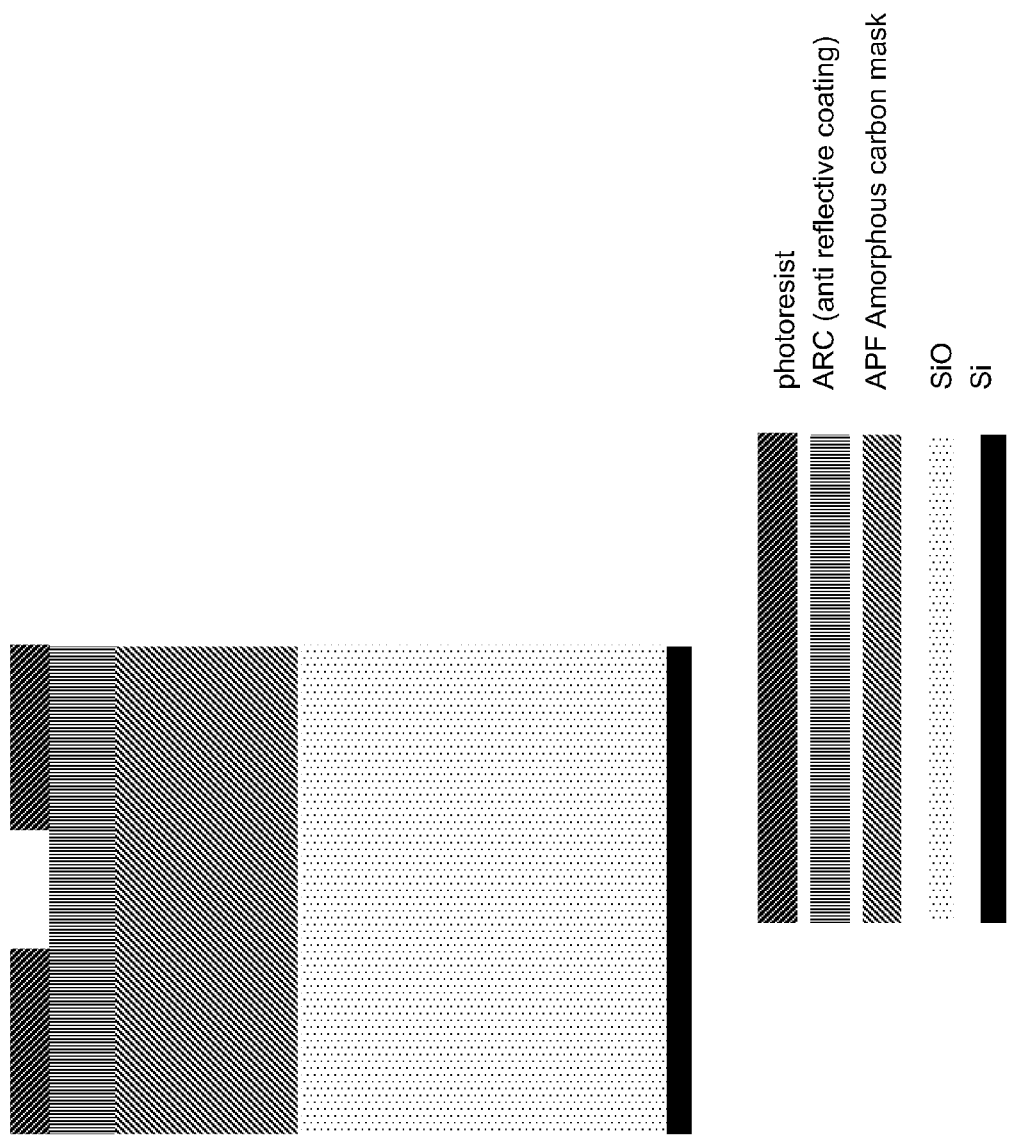
FIG. 2 is a diagram showing exemplary layers in a DRAM stack.

Alternatively, the substrate may include a stack of multiple layers thereon similar to those shown in FIG. 2. In FIG. 2, a stack of four layers is located on top of a silicon wafer substrate. An amorphous carbon mask layer is located on top of a large SiO layer. An antireflective coating layer is located on top of the amorphous carbon mask. A pattern photoresist layer is located on top of the antireflective coating. The stack of layers in FIG. 2 reflects layers similar to those used to produce a DRAM memory. One of ordinary skill in the art will recognize that the stack of layers in FIG. 2 is provided for exemplary purposes only and that the disclosed sulfur-containing compounds may be used to etch other stacks of layers. Furthermore, one of ordinary skill in the art will recognize that the number of layers in the stack may vary (i.e., may include more or less than the four layers depicted).

The vapor of the disclosed sulfur-containing compound is introduced into the chamber containing the substrate and silicon-containing layers. The vapor may be introduced to the chamber at a flow rate ranging from approximately 0.1 sccm to approximately 1 slm. For example, for a 200 mm wafer size, the vapor may be introduced to the chamber at a flow rate ranging from approximately 5 sccm to approximately 50 sccm. Alternatively, for a 450 mm wafer size, the vapor may be introduced to the chamber at a flow rate ranging from approximately 25 sccm to approximately 250 sccm. One of ordinary skill in the art will recognize that the flow rate will vary from tool to tool.

The disclosed sulfur-containing compounds may be supplied either in neat form or in a blend with a suitable solvent, such as ethyl benzene, xylenes, mesitylene, decane, or dodecane. The disclosed sulfur-containing compounds may be present in varying concentrations in the solvent. The vapor form of the sulfur-containing compounds may be produced by vaporizing the neat or blended sulfur-containing compounds solution through a conventional vaporization step such as direct vaporization or by bubbling. The neat or blended S-containing compounds may be fed in liquid state to a vaporizer where it is vaporized before it is introduced into the reactor. Alternatively, the neat or blended S-containing compounds may be vaporized by passing a carrier gas into a container containing the disclosed S-containing compounds or by bubbling the carrier gas into the disclosed S-containing compounds. The carrier gas may include, but is not limited to, Ar, He, $N_2$, and mixtures thereof. Bubbling with a carrier gas may also remove any dissolved oxygen present in the neat or blended S-containing compounds solution. The carrier gas and disclosed S-containing compounds are then introduced into the reactor as a vapor.

If necessary, the container containing the disclosed S-containing compounds may be heated to a temperature that permits the S-containing compounds to be in liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of S-containing compound vaporized.

The vapor of the disclosed S-containing compounds is activated by plasma to produce an activated vapor. The plasma decomposes the S-containing compound into radical form (i.e., the activated S-containing compound). The plasma may be generated by applying RF or DC power. The plasma may be generated with a RF power ranging from about 25 W to about 10,000 W. The plasma may be generated or present within the reactor itself. The plasma may be generated in Dual CCP or ICP mode with RF applied at both electrodes. RF frequency of plasma may range from 200 KHz to 1 GHz. Different RF sources at different frequency can be coupled and applied at same electrode. Plasma RF pulsing may be further used to control molecule fragmentation and reaction at substrate. One of skill in the art will recognize methods and apparatus suitable for such plasma treatment.

An inert gas is also introduced into the reactor in order to sustain the plasma. The inert gas may be He, Ar, Xe, Kr, Ne, or combinations thereof. The vapor of the S-containing compound and the inert gas may be mixed prior to introduction to the chamber, with the inert gas comprising between approximately 50% v/v and approximately 95% v/v of the resulting mixture. Alternatively, the inert gas may be introduced to the chamber continuously while the vapor of the S-containing compound is introduced to the chamber in pulses.

Quadropole mass spectrometer, optical emission spectrometer, FTIR, or other radical/ion measurement tools may measure the activated vapor to determine the types and numbers of species produced. If necessary, the flow rate of the vapor and/or the inert gas may be adjusted to increase or decrease the number of radical species produced.

The disclosed S-containing compounds may be mixed with other gases either prior to introduction into the reaction chamber or inside the reaction chamber. Preferably, the gases may be mixed prior to introduction to the chamber in order to provide a uniform concentration of the entering gas. In another alternative, the vapor of the S-containing compound may be introduced into the chamber independently of the other gases such as when two or more of the gases react.

Exemplary gases include, without limitation, oxidizers such as $O_2$, $O_3$, CO, $CO_2$, NO, $N_2O$, $NO_2$, and combinations thereof. The vapor of the S-containing compound and the oxidizer may be mixed together prior to introduction into the chamber. Alternatively, the oxidizer may be introduced continuously into the chamber and the vapor of the S-containing compound introduced into the chamber in pulses. The oxidizer may comprise between approximately 5% v/v to approximately 100% v/v of the mixture introduced into the chamber (with 100% v/v representing introduction of pure oxidizer for the continuous introduction alternative).

Other exemplary gases with which the vapors of the S-containing compounds may be mixed include additional etching gases, such as $cC_4F_8$, $C_4F_8$, $C_4F_6$, $CF_4$, $CH_3F$, $CF_3H$, $CH_2F_2$, COS, $CS_2$; $CF_3I$; $C_2F_3I$; $C_2F_5I$; $SO_2$; trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); or hexafluorocyclobutane (cis-1,1,2,2,3,4). The vapor of the S-containing compound and the etching gas may be mixed prior to introduction to the chamber. The etching gas may comprise between approximately 1% v/v to approximately 99.9% v/v of the mixture introduced into the chamber.

The Si-containing layers and the activated vapor react to form volatile species that are removed from the reactor. The amorphous carbon mask, antireflective coating, and photoresist layer may be less reactive with the vapor of the disclosed sulfur-containing compound.

The temperature and the pressure within the reactor are held at conditions suitable for the silicon-containing layer to react with the activated S-containing gas. For instance, the pressure in the reactor may be held between approximately 0.1 mTorr and approximately 1000 Torr, preferably between approximately 1 mTorr and approximately 10 Torr, more preferably between approximately 10 mTorr and approximately 1 Torr, and more preferably between approximately 10 mTorr and approximately 100 mTorr, as required per the etching parameters. Likewise, the substrate temperature in the reactor may range between about approximately −196° C. to approximately 500° C., preferably between −120° C. to approximately 300° C., and more preferably between −10° C. to approximately 40° C. Chamber wall temperatures may range from approximately −196° C. to approximately 300° C. depending on the process requirements.

The reactions between the Si-containing layer and the plasma activated S-containing compound results in removal of the Si-containing layer from the substrate. Atoms of nitrogen, oxygen, and/or carbon may also be present in the Si-containing layer. The removal is due to a physical sputtering of Si-containing layer from plasma ions (accelerated by the plasma) and/or by chemical reaction of plasma species to convert Si to volatile species, such as $SiF_x$, wherein x ranges from 1-4.

The plasma activated vapor of the S-containing compound preferably exhibits high selectivity toward the mask and etches through the alternating layers of SiO and SiN resulting in a vertical etch profile with no bowing, which is important for 3D NAND applications. For other applications, such as DRAM and 2D NAND, for example, the plasma activated vapor of the S-containing compound may selectively etch SiO from SiN. The plasma activated vapor of the S-containing compound preferably selectively etches SiO and/or SiN from mask layers, such as amorphous carbon, photoresist, polysilicon, or silicon carbide; or from metal contact layers, such as Cu; or from channel regions consisting of SiGe or polysilicon regions.

The disclosed etch processes using the disclosed S-containing compounds produce channel holes, gate trenches, staircase contacts, capacitor holes, contact holes, etc., in the Si-containing layers. The resulting aperture may have an aspect ratio ranging from approximately 10:1 and approximately 100:1 and a diameter ranging from approximately 40 nm to approximately 50 nm. For example, one of ordinary skill in the art will recognize that a channel hole etch produces apertures in the Si-containing layers having an aspect ratio greater than 60:1.

In one non-limiting exemplary plasma etch process, the vapor of $C_2F_3H_3S$ is introduced into a 200 mm Dual CCP plasma etch tool using a controlled gas flow device. The device may be a mass flow controller or a bubbler design with inert gas flow to deliver the vapor of the desired molecule. In case of high boiling point molecules, special low pressure drop mass flow controller from Brooks Automation (No. GF120XSD), MKS Instruments, etc., may be used. The pressure of the plasma etch tool is set at approximately 30 mTorr. No gas source heating is necessary, as the vapor pressure of this compound is approximately 400 torr at room temperature. The distance between the two CCP electrodes is kept at 1.35 cm and the top electrode RF power is fixed at 750 W. The bottom electrode RF power is varied to analyze the performance of the molecule. The plasma etch tool includes a chamber containing a substrate having Si-containing layers thereon. Argon is independently introduced into the chamber at a 250 sccm flow rate. $C_2H_3F_3S$ is independently introduced into the chamber at 15 sccm. $O_2$ is independently introduced into the chamber at 0-20 sccm to determine optimum etching conditions.

EXAMPLES

The following non-limiting examples are provided to further illustrate embodiments of the invention. However, the examples are not intended to be all inclusive and are not intended to limit the scope of the inventions described herein.

Example 1

Figure 3:
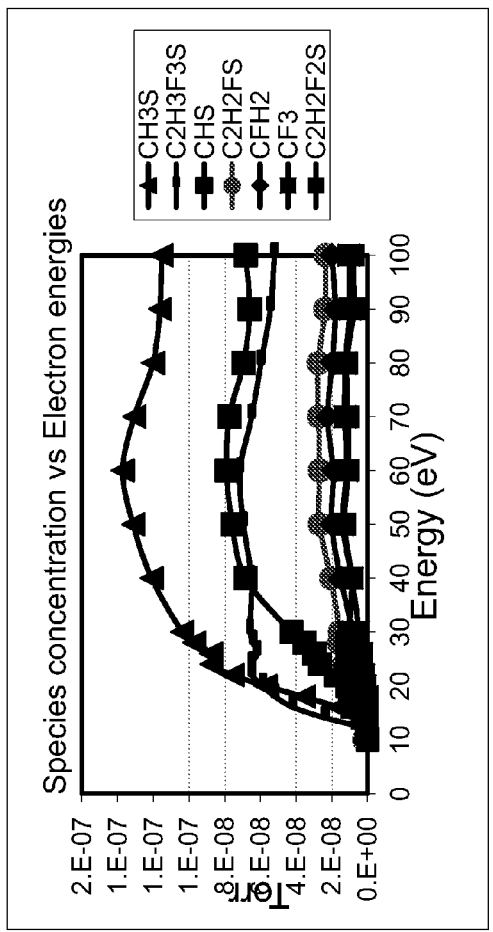
FIG. 3 is a mass spectrometry (MS) graph plotting the volume of species fractions produced by $C_2H_3F_3S$ (in Torr) versus energy (in eV)

Analysis of $C_2H_3F_3S$ (2,2,2-trifluoroethanethiol or $F_3C$—$CH_2$—SH) purchased from Sigma Aldrich was performed by mass spectrometry (MS) to study the electron impact ionization. The $C_2H_3F_3S$ etchant flowed through a mass spectrometer chamber and a quadrupole mass spectrometer (Hiden Analytical Inc.) detector studied the fragments from the etch gas as a function of electron energy. The resulting MS graph plotting the volume of plasma species fractions (Torr) versus energy (eV) is shown in FIG. 3. FIG. 3 shows that the major fragments for $C_2H_3F_3S$ are $CH_3S$ and CHS. These fragments lack fluorine and are therefore readily polymerize upon reaching the substrate.

Materials compatibility tests were also performed on $C_2H_3F_3S$. Vapor of $C_2H_3F_3S$ was introduced into and isolated in an evacuated stainless steel container having samples of stainless steel, nickel, aluminum, PCTFE (polychlorotrifluoroethylene), PVDF (polyvinylidine fluoride), and PTFE (polytetrafluoroethylene) therein. The pressure in the container after isolation was therefore approximately the vapor pressure of $C_2H_3F_3S$ (0.55 bar at 20° C.). The container was maintained at this pressure and room temperature for one month. No degradation of the samples was observed.

Example 2

Figure 4:
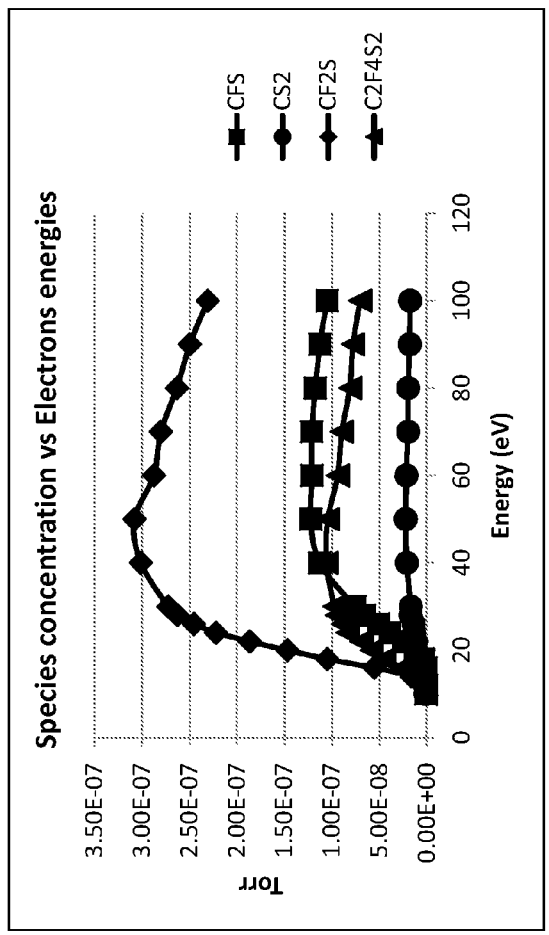
FIG. 4 is a MS graph plotting the volume of species fractions produced by $C_2F_4S_2$ (in Torr) versus energy (in eV)

Analysis of $C_2F_4S_2$ (2,2,4,4-tetrafluoro-1,3-dithietane) purchased from SynQuest was performed by mass spectrometry (MS) to study the electron impact ionization. The $C_2F_4S_2$ etchant flowed through the same mass spectrometer chamber and quadrupole mass spectrometer detector used in Example 1 to study the fragments from the etch gas as a function of electron energy. The resulting MS graph plotting the volume of plasma species fractions (Torr) versus energy (eV) is shown in FIG. 4. FIG. 4 shows that the major fragments for $C_2F_4S_2$ are CFS and $CF_2S$. These fragments have sulfur in the fragment and may therefore polymerize upon reaching the substrate.

Comparative Example 1

MS analysis of $C_2F_6S_2$ (bis(trifluoromethyl)disulfide) purchased from Synquest was performed to study the electron impact ionization. The $C_2F_6S_2$ etchant flowed through the same mass spectrometer chamber and quadrupole mass spectrometer (Hiden Analytical Inc.) detector used in Examples 1 and 2 to study the fragments from the etch gas as a function of electron energy. The resulting MS graph plotting the volume of plasma species fractions (Torr) versus energy (eV) is shown in FIG. 5.

Figure 5:
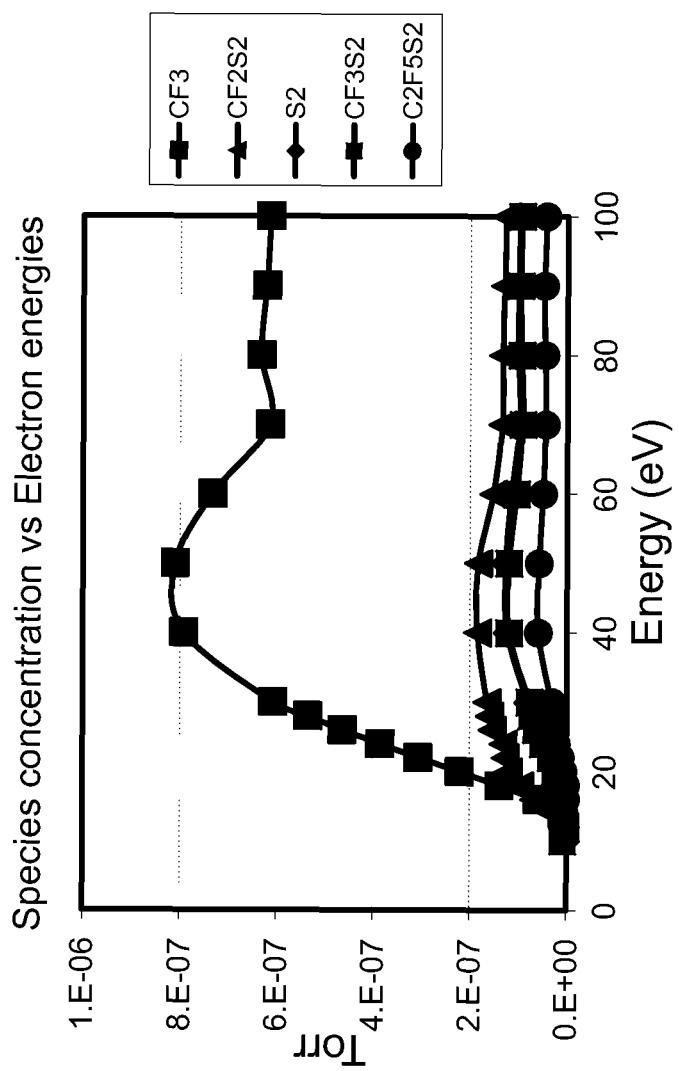
FIG. 5 is a comparative MS graph plotting the volume of species fractions produced by $C_2F_6S_2$ (in Torr) versus energy (in eV)

Comparing FIGS. 3 and 4 to FIG. 5, a larger abundance of sulfur containing fragments was generated by $C_2H_3F_3S$ and $C_2F_4S_2$ than by $C_2F_6S_2$. This means that $C_2H_3F_3S$ and $C_2F_4S_2$ will provide more sulfur containing plasma species with improved passivation film on the planar and vertical layers during plasma etch process. The sulfur film being more etch resistant to etch may lead to a better etch profile and allow high aspect ratio etching.

Additionally, a F:C ratio of ranging from 0.1:1 to 3:1 is desired for enhanced polymer formation on the sidewalls of the structure being etched (see FIG. 1a). The mass spectrometer species for both $C_2H_3F_3S$ and $C_2F_4S_2$ shows a lower F:C ratio in comparison with the species for $C_2F_6S_2$. As a result, these two molecules may favor stronger polymer characteristics.

Materials compatibility tests were also performed on $C_2F_6S_2$. Vapor of $C_2F_6S_2$ was introduced into and isolated in an evacuated stainless steel container having samples of stainless steel, nickel, aluminum, PCTFE (polychlorotrifluoroethylene), PVDF (polyvinylidine fluoride), and PTFE (polytetrafluoroethylene) therein. The pressure in the container after isolation was therefore approximately the vapor pressure of $C_2F_6S_2$ (0.6 bar at 20° C.). The container was maintained at this pressure and room temperature for one month. No degradation of the samples was observed.

Example 3

Plasma vapor deposition testing was performed with $C_2H_3F_3S$ on 1×1 cm² Si coupons. The testing was performed in a commercial LAM 4520 XLE etcher, schematically shown in FIG. 6. The etcher is a dual frequency capacitively coupled plasma reactor equipped with two 8 inch electrodes that allows independent control of number density and ion energy. The upper electrode was connected to a 27 MHz power supply (source power), that allows independent control of number density. The Si coupon was placed on the temperature controlled bottom electrode connected to a 2 MHz power supply (bias power) that allows independent control of ion energy. A 8 inch silicon showerhead on the upper electrode allowed a uniform distribution of the feed gas during plasma processes.

15 sccm $C_2H_3F_3S$ via 250 sccm of Ar gas was introduced through the showerhead for 60 seconds into the etcher having 750 W/0 W bias, 30 mTorr pressure, and a 1.35 cm gap between the top surface of the electrostatic chuck and the bottom surface of the showerhead. A 90 nm polymer film was deposited on the Si coupon (measured at 3 points by Scanning Electron Microscope (SEM)). As a result, the deposition rate was approximately 90 nm/minute. The sample was sent for X-ray photoelectron spectroscopy (XPS) analysis. The resulting XPS graph plotting an atom's electron binding energy on the X axis versus the count (number of electrons detected) on the Y axis is shown in FIG. 7. The wide scan elemental analysis of FIG. 7 shows the presence of C, F, O, and S peaks, and more particularly a S 2s peak at approximately 228 ev and a S 2p peak at approximately 164 eV.

Some portion of the deposited film included a powdery material (see FIGS. 8A and 8B). The uniform film deposited can be seen below the powder particle in FIGS. 8A and 8B. Even when bias power of 1500 W is applied, when no oxygen is added, powdery material was observed on the Si wafer. One of ordinary skill in the art will recognize that the polymer and powder formation may be controlled by changing process parameters, such as bias power and/or oxygen flow rate.

Example 4

Plasma vapor deposition testing was performed with $C_2F_4S_2$ on 1×1 cm$^2$ Si coupons. The testing was performed in the same commercial LAM 4520 XLE etcher used in Example 3 and schematically shown in FIG. 6. The upper electrode was connected to a 27 MHz power supply (source power), that allows independent control of number density. The Si coupon was placed on the temperature controlled bottom electrode connected to a 2 MHz power supply (bias power) that allows independent control of ion energy. A 8 inch silicon showerhead on the upper electrode allowed a uniform distribution of the feed gas during plasma processes.

15 sccm $C_2F_4S_2$ via 250 sccm of Ar gas was introduced through the showerhead for 60 seconds into the etcher having 750 W/0 W bias, 30 mTorr pressure, and a 1.35 cm gap between the top surface of the electrostatic chuck and the bottom surface of the shower head. A 75 nm polymer film was deposited on the Si coupon (measured at 3 points by SEM). As a result, the deposition rate was approximately 75 nm/minute.

Comparative Example 2

Figure 6:
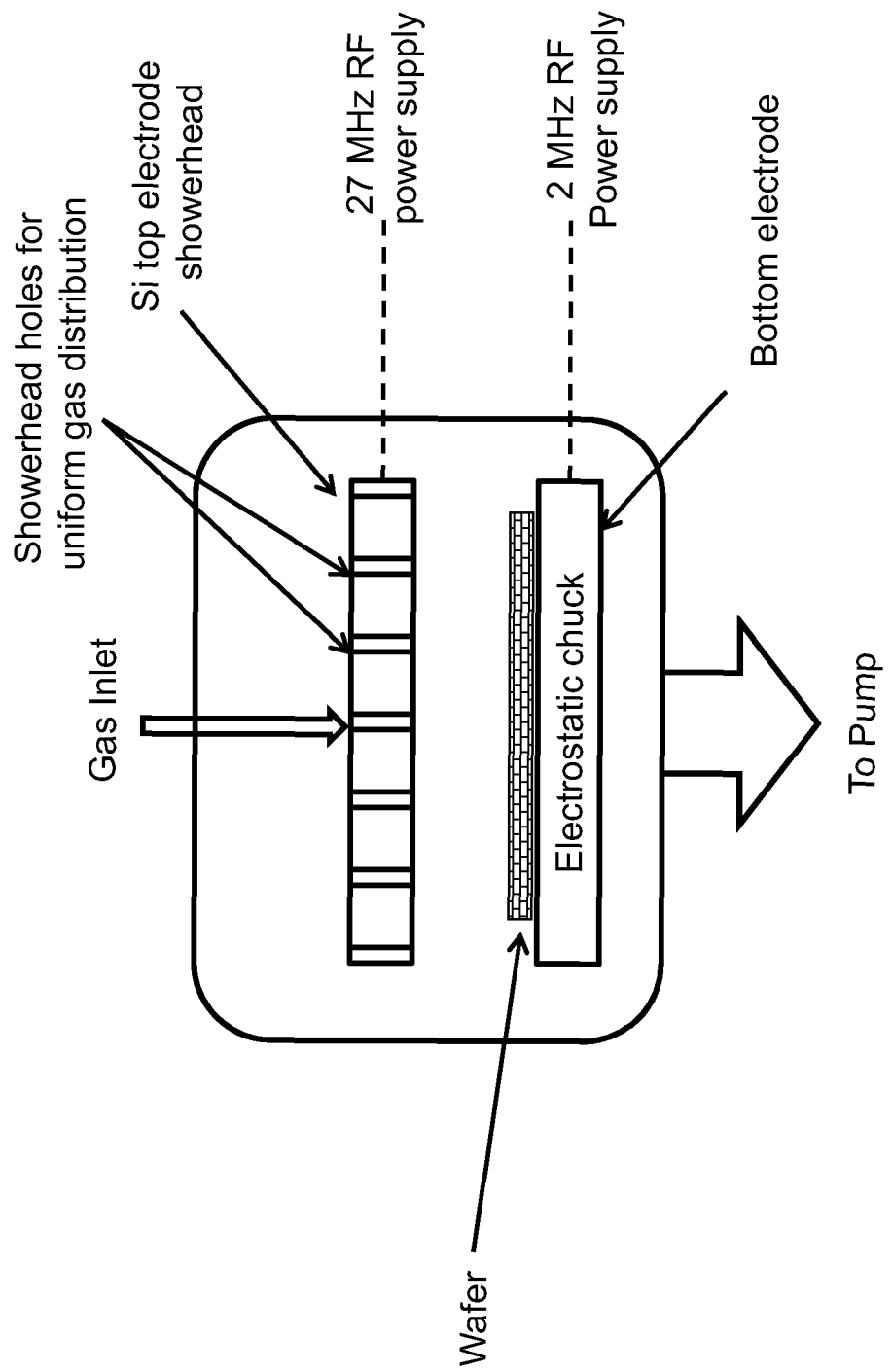
FIG. 6 is a schematic drawing of the etcher used in the examples that follow.
Figure 9:
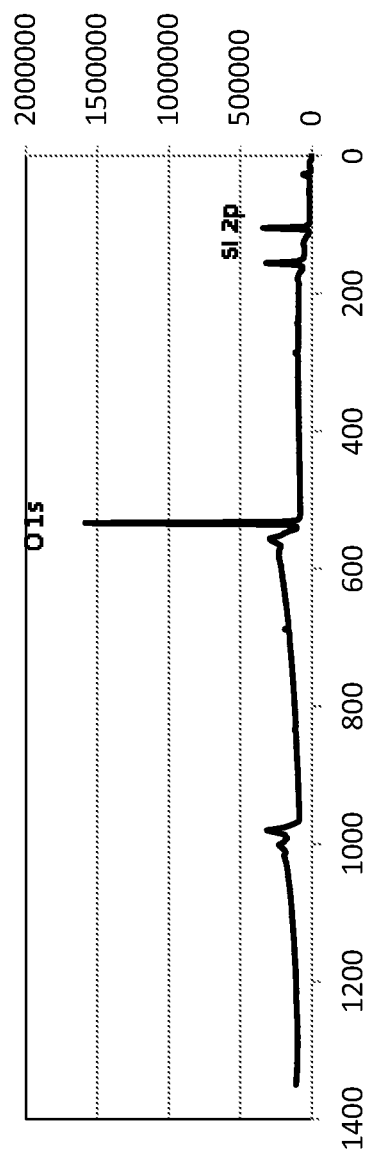
FIG. 9 is a XPS graph of the atoms in the Si coupon on which an attempt was made to deposit a polymer from $C_2F_6S_2$.

Plasma vapor deposition testing was performed with $C_2F_6S_2$ on 1×1 cm$^2$ Si coupons. 15 sccm $C_2F_6S_2$ via 250 sccm of Ar gas was introduced for 60 seconds into the etcher of FIG. 6 having 750 W/0 W bias, 30 mTorr pressure, and a 1.35 cm gap. No film was deposited. The sample was sent for XPS analysis. The resulting XPS graph is shown in FIG. 9, showing only Si and O peaks, and more particularly a Si 2s peak at approximately 156 ev and a Si 2p peak at approximately 105 eV. No evidence of either C or S in FIG. 9 indicates that no protective polymer was formed. The lack of deposition will not provide sufficient passivation during the plasma etch process and therefore may lead to high bowing in the etched structures. As a result, the $C_2F_6S_2$ etchant will not be useful for applications that require profile control or sidewall passivation.

Example 5

Etching experiments were performed with $C_2H_3F_3S$ on four 1×1 cm$^2$ coupons that were glued to the 200 mm Si carrier wafer using double sided carbon tape. The four substrate materials investigated were Silicon oxide ($SiO_2$), Silicon Nitride (SiN), polysilicon (p-Si), and amorphous carbon (a-C). The etching tests were performed in the etcher of FIG. 6 set at a pressure of 30 mTorr, source power of 750 W (27 MHz), and bias power of 1500 W (2 MHz). The feed mixture contained 250 sccm of Ar and 15 sccm of $C_2H_3F_3S$. The oxygen ($O_2$) flow rate varied from 0 to 15 sccm. The etch rates were measured using an ellipsometer and the deposition rates were measured by SEM by measuring the change in film thickness as a function of process time.

Figure 10:
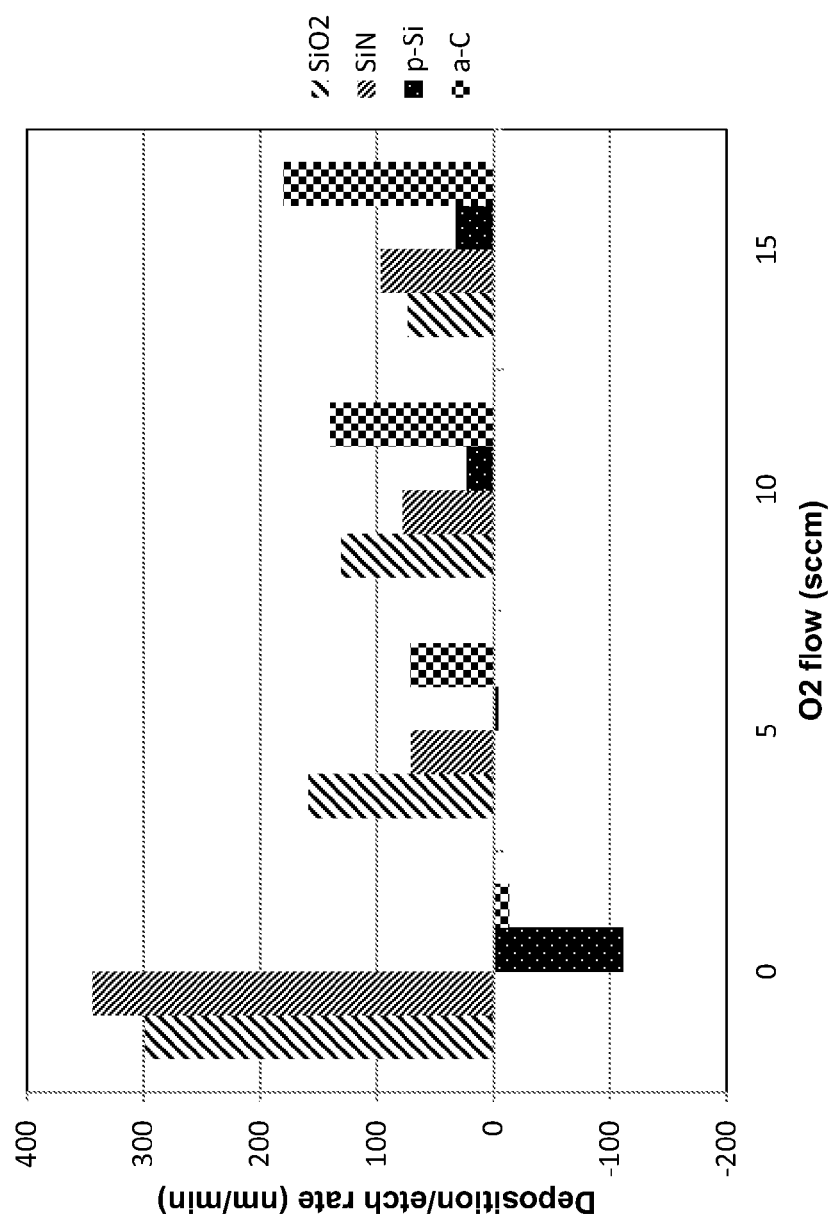
FIG. 10 is a graph of the etch rates of $C_2H_3F_3S$ on $SiO_2$, SiN, p-Si and a-C plotted as a function of oxygen flow rate.

The resulting etch rates of $SiO_2$, SiN, p-Si and a-C using $C_2H_3F_3S$ are plotted as a function of oxygen flow rate in sccm and are presented in FIG. 10. The positive y-axis represents etch rates while the negative y-axis represents deposition rates. The x-axis is $O_2$ flow in sccm. As oxygen is added, the $SiO_2$:a-C selectivity drops drastically and there is a condition where a-C etch rates are higher than those for the $SiO_2$ and SiN films.

As illustrated in FIG. 10, when no oxygen is added (0 sccm $O_2$ condition), the etch rates of $SiO_2$ and SiN are close to one another (with Selectivity ~1:1, and etch rate of ~300 nm/min), while uniform deposition (no powder) is seen on the p-Si and a-C substrates. As a result, this compound may be suitable for the 3D NAND process, which requires the etch rates of $SiO_2$ and SiN to be similar and the etch rates of p-Si and a-C to be low. The similar etch rates for $SiO_2$ and SiN may result in less bowing and faceting. The low etch rates for p-Si and a-C may help to preserve the mask material. However, the etch rates of $SiO_2$ and SiN are lower than those for the standard $cC_4F_8$ gas (above 550 nm/min). Additional etch gases, such as $CF_4$, may be added to increase the etch rate (see Example 6).

Comparative Example 3

Figure 13:
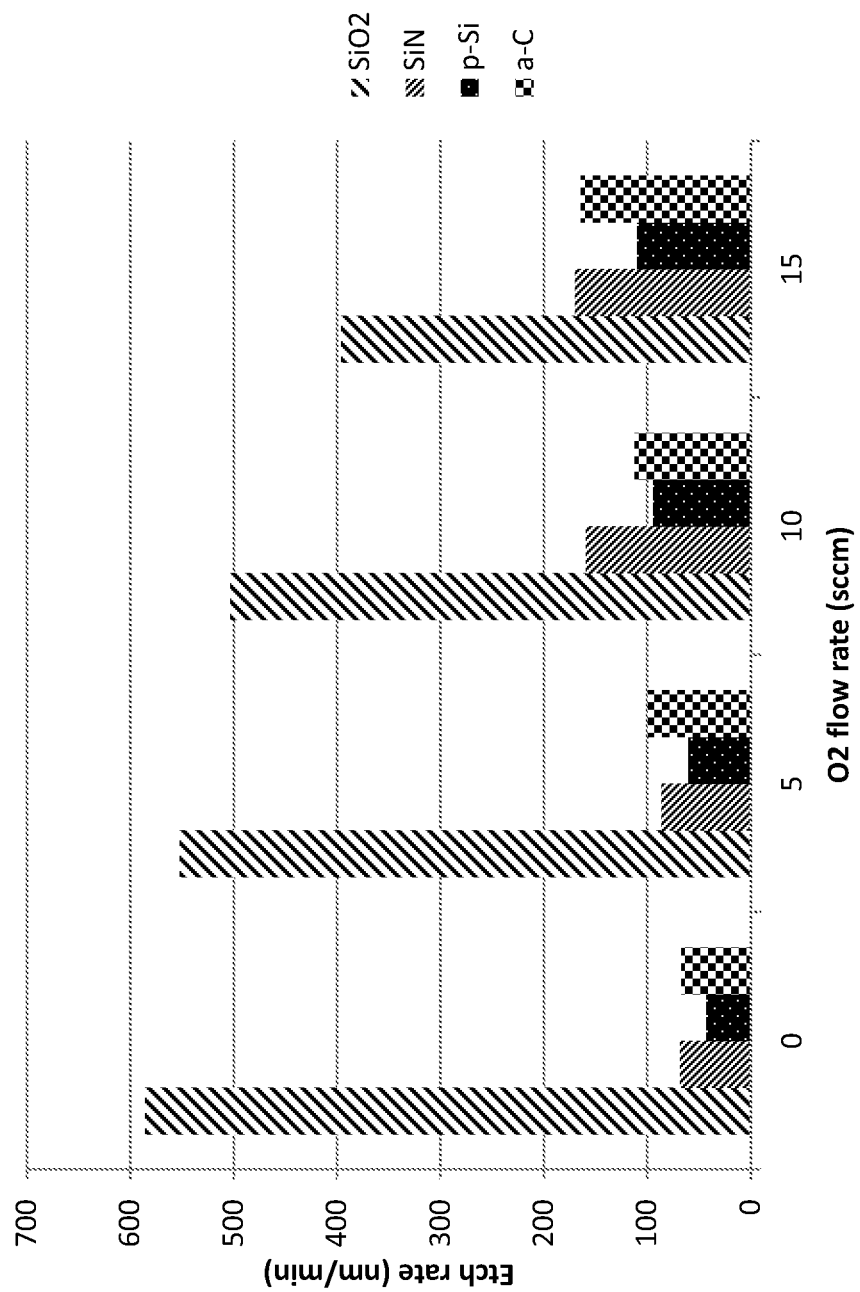
FIG. 13 is a graph of the etch rates of $cC_4F_8$ on $SiO_2$, SiN, p-Si and a-C plotted as a function of oxygen flow rate.

Etching experiments were performed with $cC_4F_8$ as a function of $O_2$ flowrate, under similar process conditions described in Example 5. The results are shown in FIG. 13. As illustrated in FIG. 13, the selectivity of $SiO_2$ and SiN with respect to p-Si and a-C is lower than $C_2H_3F_3S$ when no oxygen is added.

Comparative Example 4

Figure 14:
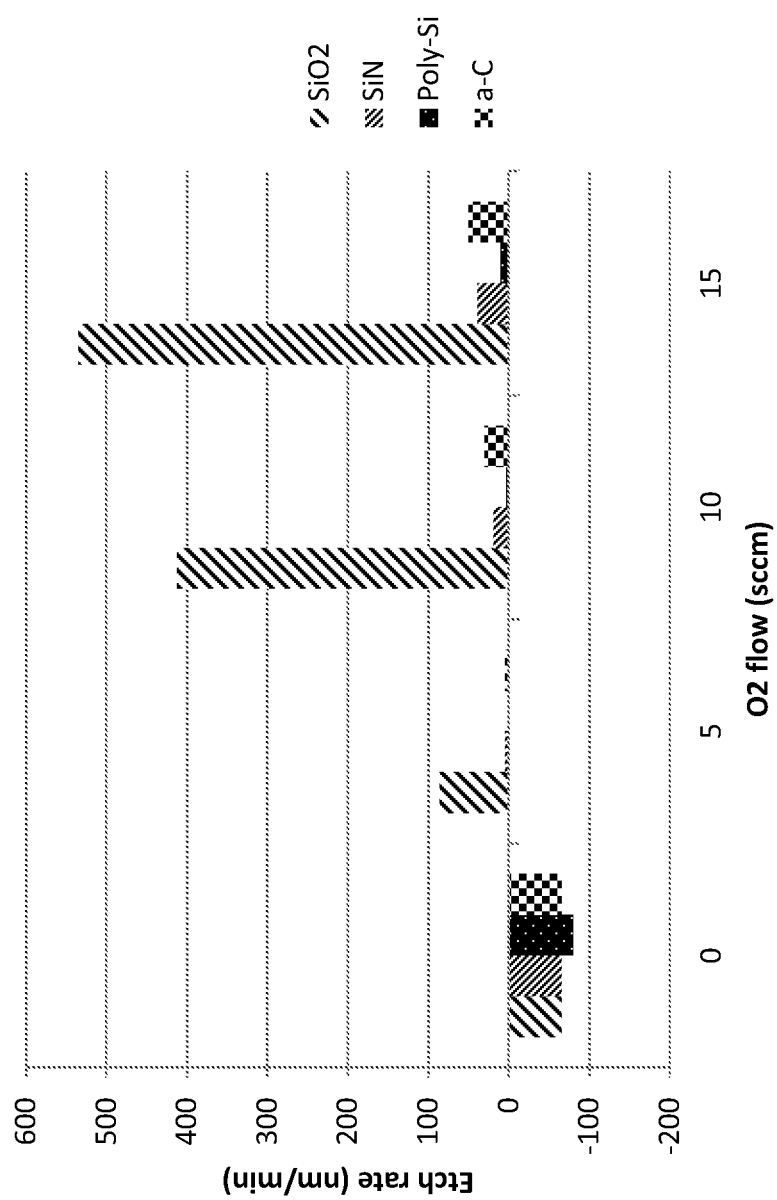
FIG. 14 is a graph of the etch rates of $C_4F_6$ on $SiO_2$, SiN, p-Si and a-C plotted as a function of oxygen flow rate.

Etching experiments were performed with $C_4F_6$ as a function of $O_2$ flowrate, under similar process conditions described in Example 5. The results are shown in FIG. 14. As illustrated in FIG. 14, the selectivity of $SiO_2$ and SiN with respect to p-Si and a-C is higher for $C_4F_6$ than it is for $C_2H_3F_3S$. However, the $SiO_2$:SiN selectivity of $C_4F_6$ is higher than it is in Example 5, making $C_4F_6$ less suitable for some applications. The $C_2H_3F_3S$ molecule, on the other hand, gives similar etch rates for $SiO_2$ and SiN, when no oxygen is added, as shown in FIG. 10.

Example 6

Figure 11:
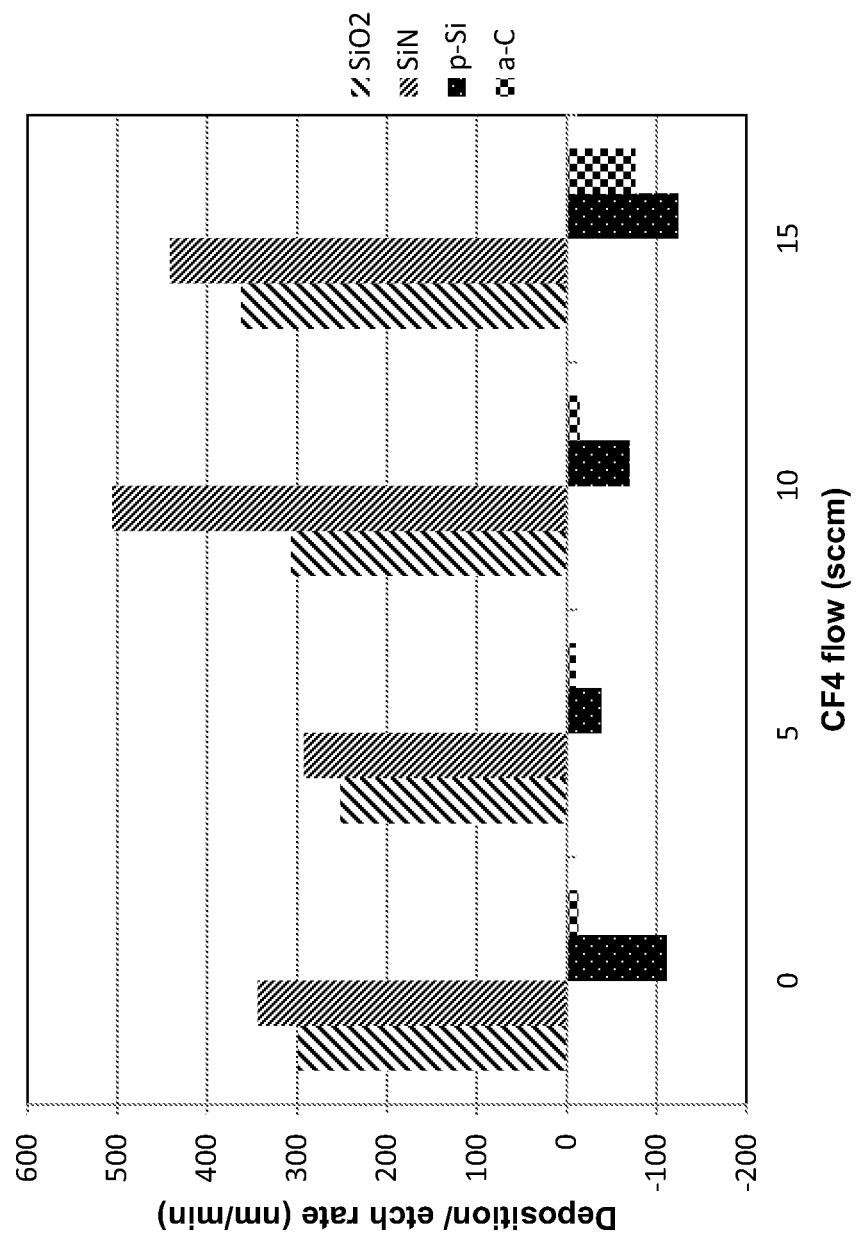
FIG. 11 is a graph of the etch rates of the combination of $C_2H_3F_3S$ with $CF_4$ on $SiO_2$, SiN, p-Si and a-C plotted as a function of $CF_4$ flow rate.

In order to improve the $C_2H_3F_3S$ etch rates of the $SiO_2$/SiN films to be comparable to the performance of $cC_4F_8$, $CF_4$ was added to the etch gas mixture of 250 sccm Ar and 15 sccm $C_2H_3F_3S$. The $CF_4$ addition varied from 0 to 15 sccm. As illustrated in FIG. 11, adding $CF_4$ to the process gas mixture increases the etch rates of $SiO_2$/SiN to 400 nm/min and above, while maintaining the selectivity to p-Si and a-C, making this an excellent molecule for 3D NAND application.

Comparative Example 5

Figure 15:
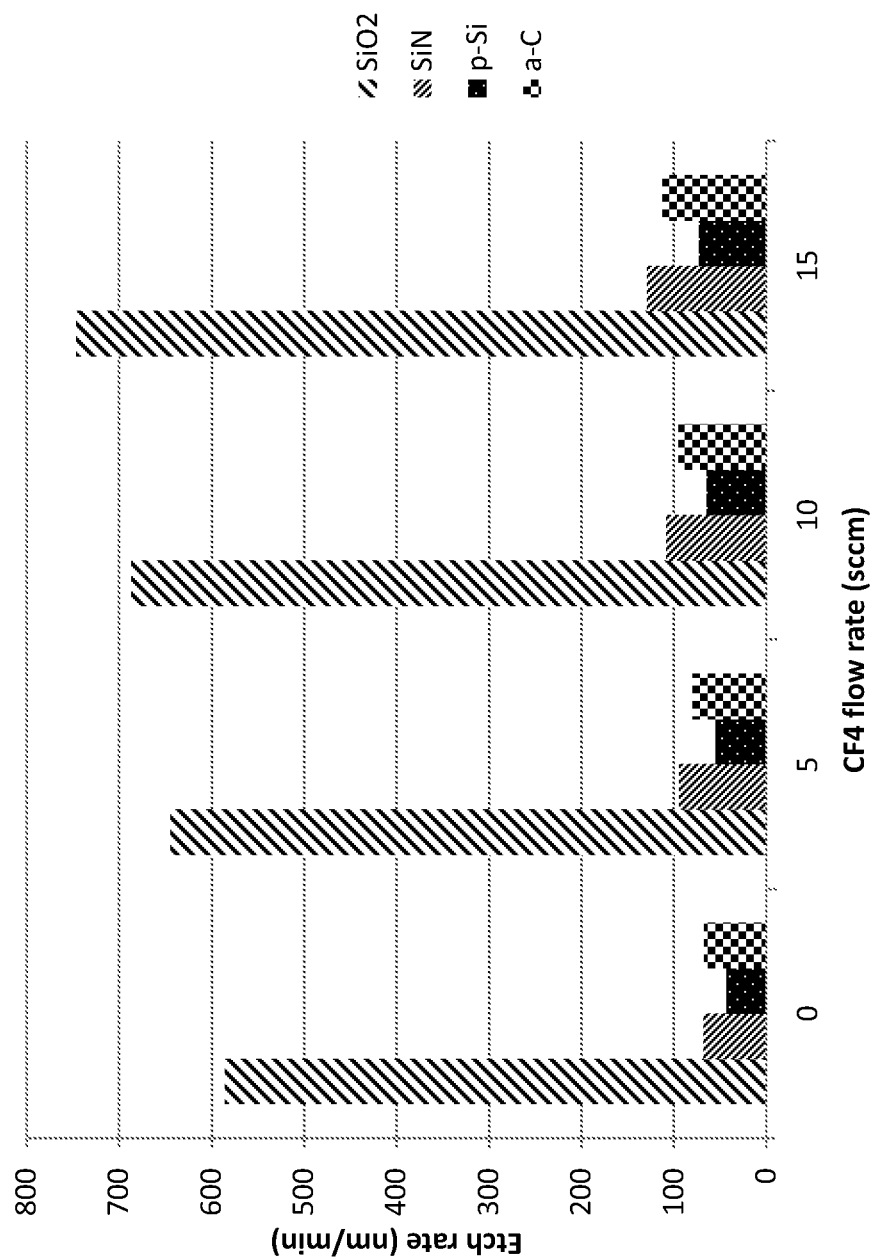
FIG. 15 is a graph of the etch rates of the combination of $cC_4F_8$ with $CF_4$ on $SiO_2$, SiN, p-Si and a-C plotted as a function of $CF_4$ flow rate.

Etching experiments were also performed where $CF_4$ was added to the etch gas mixture of 250 sccm Ar and 15 sccm $cC_4F_8$ and results are shown in FIG. 15. As illustrated in FIG. 15, the etch rates of all the four substrates increased and as a result no improvement in selectivity is obtained. On the other hand, using $C_2H_3F_3S$, the etch rates of $SiO_2$ and SiN are increased thus increasing selectivity to p-Si and a-C.

Example 7

Etching experiments were performed with $C_2F_4S_2$ on four 1×1 cm² coupons that were glued to the 200 mm Si carrier wafer using double sided carbon tape. The four substrate materials investigated were Silicon oxide ($SiO_2$), Silicon Nitride (SiN), polysilicon (p-Si), and amorphous carbon (a-C). The etching tests were performed in the etcher of FIG. 6 set at a pressure of 30 mTorr, source power of 750 W (27 MHz), and bias power of 1500 W (2 MHz). The feed mixture contained 250 sccm of Ar and 15 sccm of $C_2F_4S_2$. The oxygen ($O_2$) flow rate varied from 0 to 15 sccm. The etch rates were measured using an ellipsometer and the deposition rates were measured using SEM by measuring the change in film thickness as a function of process time.

Figure 12:
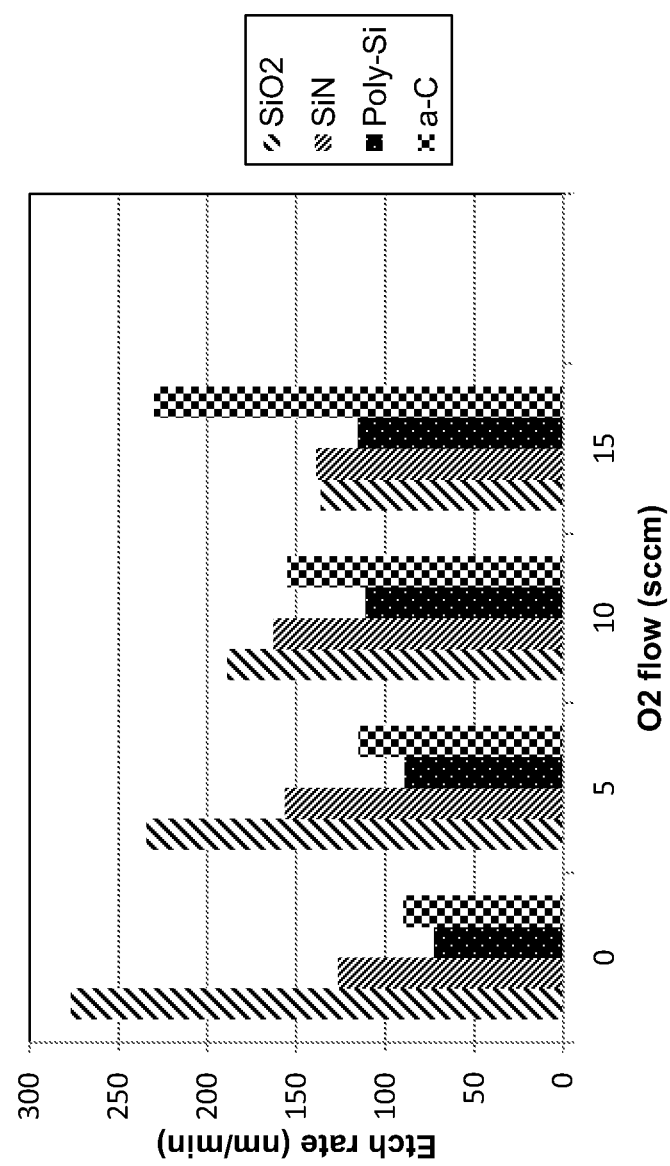
FIG. 12 is a graph of the etch rates of $C_2F_4S_2$ on $SiO_2$, SiN, p-Si and a-C plotted as a function of oxygen flow rate.

The resulting etch rates of $SiO_2$, SiN, p-Si and a-C using $C_2F_4S_2$ are plotted as a function of oxygen flow rate in sccm and are presented in FIG. 12. The positive y-axis represents etch rates while the negative y-axis represents deposition rates. The x-axis is $O_2$ flow in sccm. As the oxygen flow rate increases, the etch rate of $SiO_2$ decreases while the etch rates for p-Si and a-C increases. As a result, the selectivity of $SiO_2$ to a-C and p-Si decreases with increased oxygen flow rates.

As illustrated in FIG. 12, the etch rates for $SiO_2$, SiN and p-Si are approximately the same at a 15 sccm $O_2$ flow rate. This may indicate that $C_2F_4S_2$ generates free fluorine as the dominant etchant at this flow rate, making $C_2F_4S_2$ a good additive to highly polymerizing gases, such as $C_4F_6$ and $C_5F_8$.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for plasma etching a silicon-containing layer on a substrate, the method comprising,
   introducing a vapor of a compound into a chamber containing the silicon-containing layer on a substrate, the compound selected from the group consisting of: $C_2F_4S_2$ (CAS 1717-50-6), $F_3CSH$ (CAS 1493-15-8), $F_3C$—$CF_2$—SH (CAS 1540-78-9), $F_3C$—$CH_2$—SH (CAS 1544-53-2 $CHF_2$—$CF_2$—SH 812-10-2 $CF_3$—$CF_2$—$CH_2$—SH (CAS 677-57-6), $F_3C$—CH(SH)—$CF_3$ (CAS 1540-06-3), $F_3C$—S—$CF_3$ (CAS 371-78-8), $F_3C$—S—$CHF_2$ (CAS 371-72-2), $F_3C$—$CF_2$—S—$CF_2$—$CF_3$ (CAS 155953-22-3), $F_3C$—$CF_2$—$CF_2$—S—$CF_2$—$CF_3$ (CAS 356-63-8), c(-S—$CF_2$—$CF_2$—CHF—$CF_2$—) (CAS 1035804-79-5), c(-S—$CF_2$—CHF—CHF—$CF_2$—) (CAS 30835-84-8), c(-S—$CF_2$—$CF_2$—$CF_2$—$CF_2$—$CF_2$—) (CAS 24345-52-6), c(-S—CFH—$CF_2$—$CF_2$—CFH—)(2 R, 5 R) (CAS 1507363-75-8), c(-S—CFH—$CF_2$—$CF_2$—CFH—)(2 R, 5 S) (CAS 1507363-76-9), and c(-S—CFH—$CF_2$—$CF_2$—$CH_2$—) (CAS 1507363-77-0);
   introducing an inert gas into the chamber;
   generating a plasma to produce an activated vapor from the vapor; and
   removing volatile by-product from the chamber, wherein the activated vapor selectively reacts with the silicon-containing layer to form the volatile by-product.

2. The method of claim 1, wherein the compound is $C_2F_4S_2$ (CAS 1717-50-6).

3. The method of claim 1, wherein the compound is selected from the group consisting of $F_3CSH$ (CAS 1493-15-8), $F_3C$—$CF_2$—SH (CAS 1540-78-9), $F_3C$—$CH_2$—SH (CAS 1544-53-2), $CHF_2$—$CF_2$—SH (812-10-2), $CF_3$—$CF_2$—$CH_2$—SH (CAS 677-57-6), and $F_3C$—CH(SH)—$CF_3$ (CAS 1540-06-3).

4. The method of claim 1, wherein the compound is selected from the group consisting of $F_3C$—S—$CF_3$ (CAS 371-78-8), $F_3C$—S—$CHF_2$ (CAS 371-72-2), $F_3C$—$CF_2$—S—$CF_2$—$CF_3$ (CAS 155953-22-3), and $F_3C$—$CF_2$—$CF_2$—S—$CF_2$—$CF_3$ (CAS 356-63-8).

5. The method of claim 1, wherein the compound is selected from the group consisting of c(-S—$CF_2$—$CF_2$—CHF—$CF_2$—) (CAS 1035804-79-5), c(-S—$CF_2$—CHF—CHF—$CF_2$—) (CAS 30835-84-8), c(-S—$CF_2$—$CF_2$—$CF_2$—$CF_2$—$CF_2$—) (CAS 24345-52-6), c(-S—CFH—$CF_2$—$CF_2$—CFH—)(2 R, 5 R) (CAS 1507363-75-8), c(-S—CFH—$CF_2$—$CF_2$—CFH—) (2 R, 5 S) (CAS 1507363-76-9), and c(-S—CFH—$CF_2$—$CF_2$—$CH_2$—) (CAS 1507363-77-0).

6. The method of claim 1, wherein the silicon-containing layer comprises a layer of silicon oxide, silicon nitride, polysilicon, or combinations thereof.

7. The method of claim 1, further comprising introducing an oxidizer into the chamber.

8. The method of claim 7, wherein the oxidizer is selected from the group consisting of $O_2$, $O_3$, CO, $CO_2$, NO, $N_2O$, $NO_2$, and combinations thereof.

9. The method of claim 7, wherein the oxidizer is $O_2$.

10. The method of claim 1, further comprising introducing an etching gas into the chamber, wherein the etching gas is selected from the group consisting of $cC_5F_8$, $cC_4F_8$, $C_4F_8$, $C_4F_6$, $CF_4$, $CH_3F$, $CF_3H$, $CH_2F_2$, COS, $CS_2$; $CF_3I$; $C_2F_3I$; $C_2F_5I$; $SO_2$; trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); and hexafluorocyclobutane (cis-1,1,2,2,3,4).

11. The method of claim 1, wherein the compound is $F_3C$—$CH_2$—SH (CAS 1544-53-2).

12. The method of claim 1, wherein the silicon-containing layer comprises a combination of silicon oxide and silicon nitride.

13. The method of claim 12, wherein the compound is $F_3C$—$CH_2$—SH (CAS 1544-53-2).

14. The method of claim 12, wherein the compound is $C_2F_4S_2$ (CAS 1717-50-6).

15. A method for plasma etching a silicon-containing layer, the method comprising,
   introducing $F_3C$—$CH_2$—SH (CAS 1544-53-2) gas into a chamber containing the silicon-containing layer on a substrate, wherein the silicon-containing layer comprises a combination of silicon oxide and silicon nitride;

introducing an inert gas into the chamber;
plasma activating $F_3C$—$CH_2$—SH (CAS 1544-53-2) gas; and
removing volatile by-product from the chamber, wherein the plasma activated $F_3C$—$CH_2$—SH (CAS 1544-53-2) gas selectively reacts with the silicon-containing layer to form the volatile by-product.

* * * * *